(12) United States Patent
Kramer et al.

(10) Patent No.: US 6,597,951 B2
(45) Date of Patent: Jul. 22, 2003

(54) AUTOMATIC SELECTION FROM MULTIPLE CARDIAC OPTIMIZATION PROTOCOLS

(75) Inventors: Andrew P. Kramer, Stillwater, MN (US); Veerichetty Kadhiresan, Temecula, CA (US); Jiang Ding, Maplewood, MN (US); Lawrence Baumann, Bloomington, MN (US); Scott Vanderlinde, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/995,255

(22) Filed: Nov. 27, 2001

(65) Prior Publication Data

US 2002/0133198 A1 Sep. 19, 2002

Related U.S. Application Data

(63) Continuation of application No. 09/810,082, filed on Mar. 16, 2001, now abandoned.

(51) Int. Cl.[7] ............................................... A61N 1/365
(52) U.S. Cl. ............................... 607/9; 607/24; 607/25
(58) Field of Search ................................ 607/9, 18, 24, 607/25, 15; 600/516, 526

(56) References Cited

U.S. PATENT DOCUMENTS

| | | | |
|---|---|---|---|
| 5,188,106 A | * 2/1993 | Nappholz et al. | 607/24 |
| 5,312,452 A | 5/1994 | Salo | 607/17 |
| 5,318,595 A | 6/1994 | Ferek-Petric et al. | 607/17 |
| 5,334,222 A | 8/1994 | Salo et al. | 607/17 |
| 5,413,592 A | 5/1995 | Schroeppel | 607/18 |
| 5,417,717 A | * 5/1995 | Salo et al. | 607/18 |
| 5,466,245 A | 11/1995 | Spinelli et al. | 607/17 |
| 5,487,752 A | 1/1996 | Salo et al. | 607/17 |
| 5,514,163 A | 5/1996 | Markowitz et al. | 607/9 |
| 5,527,347 A | 6/1996 | Shelton et al. | 607/9 |
| 5,534,016 A | 7/1996 | Boute | 607/9 |
| 5,540,727 A | 7/1996 | Tockman et al. | 607/18 |
| 5,549,650 A | 8/1996 | Bornzin et al. | 607/24 |
| 5,554,177 A | 9/1996 | Kieval et al. | 607/17 |
| 5,584,868 A | 12/1996 | Salo et al. | 607/17 |
| 5,626,620 A | 5/1997 | Kieval et al. | 607/9 |
| 5,626,623 A | 5/1997 | Kieval et al. | 607/23 |
| 5,690,689 A | 11/1997 | Sholder | 607/24 |
| 5,700,283 A | 12/1997 | Salo | 607/17 |
| 5,713,933 A | 2/1998 | Condie et al. | 607/28 |
| 5,716,383 A | 2/1998 | Kieval et al. | 607/9 |
| 5,749,906 A | 5/1998 | Kieval et al. | 607/9 |
| 5,800,471 A | 9/1998 | Baumann | 607/25 |
| 5,836,987 A | 11/1998 | Baumann et al. | 607/17 |
| 5,891,176 A | 4/1999 | Bornzin | 607/18 |
| 6,058,329 A | 5/2000 | Salo et al. | 607/17 |
| 6,144,880 A | 11/2000 | Ding et al. | 607/23 |

* cited by examiner

Primary Examiner—Kennedy Schaetzle
(74) Attorney, Agent, or Firm—Schwegman, Lundberg Woessner & Kluth, P.A.

(57) ABSTRACT

A method and system for setting the operating parameters of a cardiac rhythm management device in which a plurality of parameter optimization algorithms are available. A measured feature of an electrophysiological signal such as QRS width has been shown to be useful in selecting among certain parameter optimization algorithms.

32 Claims, 6 Drawing Sheets

AUTOMATIC SELECTION FROM MULTIPLE CARDIAC OPTIMIZATION PROTOCOLS

CROSS REFERENCE TO RELATED APPLICATION

This application is a continuation of U.S. patent application Ser. No. 09/810,082, filed on Mar. 16, 2001, the specification of which is hereby incorporated by reference.

TECHNICAL FIELD

The present invention relates to pulse generators and in particular to the selection and control of executable protocols of the implantable pulse generator.

BACKGROUND

Cardiac rhythm management devices are devices that treat disorders of cardiac rhythm and include implantable pulse generators such as pacemakers and implantable cardioverter/defibrillators that provide electrical stimulation to selected chambers of the heart. A pacemaker, for example, is an implantable pulse generator that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Also included within the concept of cardiac rhythm is the degree to which the heart chambers contract in a coordinated manner during a cardiac cycle to result in the efficient pumping of blood. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Heart failure is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium. The resulting diminishment in cardiac output may be significant in a CHF patient whose cardiac output is already compromised. Intraventricular and/or interventricular conduction defects (e.g., bundle branch blocks) are also commonly found in CHF patients. In order to treat these problems, cardiac rhythm management devices have been developed which provide electrical pacing stimulation to one or both ventricles in an attempt to improve the coordination of ventricular contractions, termed cardiac resynchronization therapy.

SUMMARY

The present invention is a method and system for optimizing the operating parameters of a cardiac rhythm management device such as an implantable pulse generator in which a plurality of optimization algorithms are available. Such operating parameters may include, for example, the programmed AV delay and, if biventricular pacing is allowed by the physical configuration of the device, which ventricles to pace and the offset between ventricular paces. Optimization algorithms usually represent methods for setting parameter values that have empirically been shown to be effective in improving the cardiac status of at least some patients. Such algorithms reach a decision based upon various inputs including the physical configuration of the device, variables measured by the device, and patient data otherwise collected. Parameter optimization algorithms usually do not, however, produce information that is helpful in selecting which among a plurality of available algorithms is the optimum one to use in a given situation. In accordance with the invention, an indication of the degree of ventricular asynchrony existing in the patient is used to select an optimization algorithm. Other factors that may influence the selection include the physical configuration of the device and whether a selected algorithm produces parameter settings that are within allowable ranges.

In an exemplary embodiment, two parameter optimization algorithms are available. One algorithm adjusts the operating parameters in a manner that maximizes cardiac output while the other adjusts the operating parameters so as to maximize myocardial contractile functim (i.e., the strength of systolic contractions). The former may be implemented by a pulse pressure optimization algorithm since systolic pulse pressure is directly related to cardiac output at a given heart rate. An indirect way of determining pulse pressures produced by an atrial-triggered ventricular pacing mode with particular parameter settings is to measure the intrinsic atrial heart rate produced by the patient's baroreceptor reflex. The pulse pressure optimization algorithm may then recommend the best parameter settings as determined from a series of trials, where the settings may include AV delay and/or which chambers to pace. The other optimization algorithm is one that adjusts the AV delay based upon a measured intrinsic atrio-ventricular conduction time (e.g., a PR interval on an electrogram). Parameter settings produced by such an algorithm have been shown to maximize myocardial contractile functim as reflected by the rate of change of systolic pressure. In accordance with the invention, an indication of the degree of ventricular asynchrony exhibited by the patient is used to select between the two optimization algorithms in a given situation. The morphology of an intrinsic QRS complex, or its equivalent in an electrogram, can be used as one indication of ventricular asynchrony. The width of the QRS waveform, as determined either from a single representative sample or from an average of such samples, is indicative of any delays that exist in ventricular depolarization. In a particular embodiment, the pulse pressure optimization algorithm is used in preference to the contractility optimization algorithm when the QRS width indicates a relatively large degree of asynchrony.

DETAILED DESCRIPTION

Figure 1:
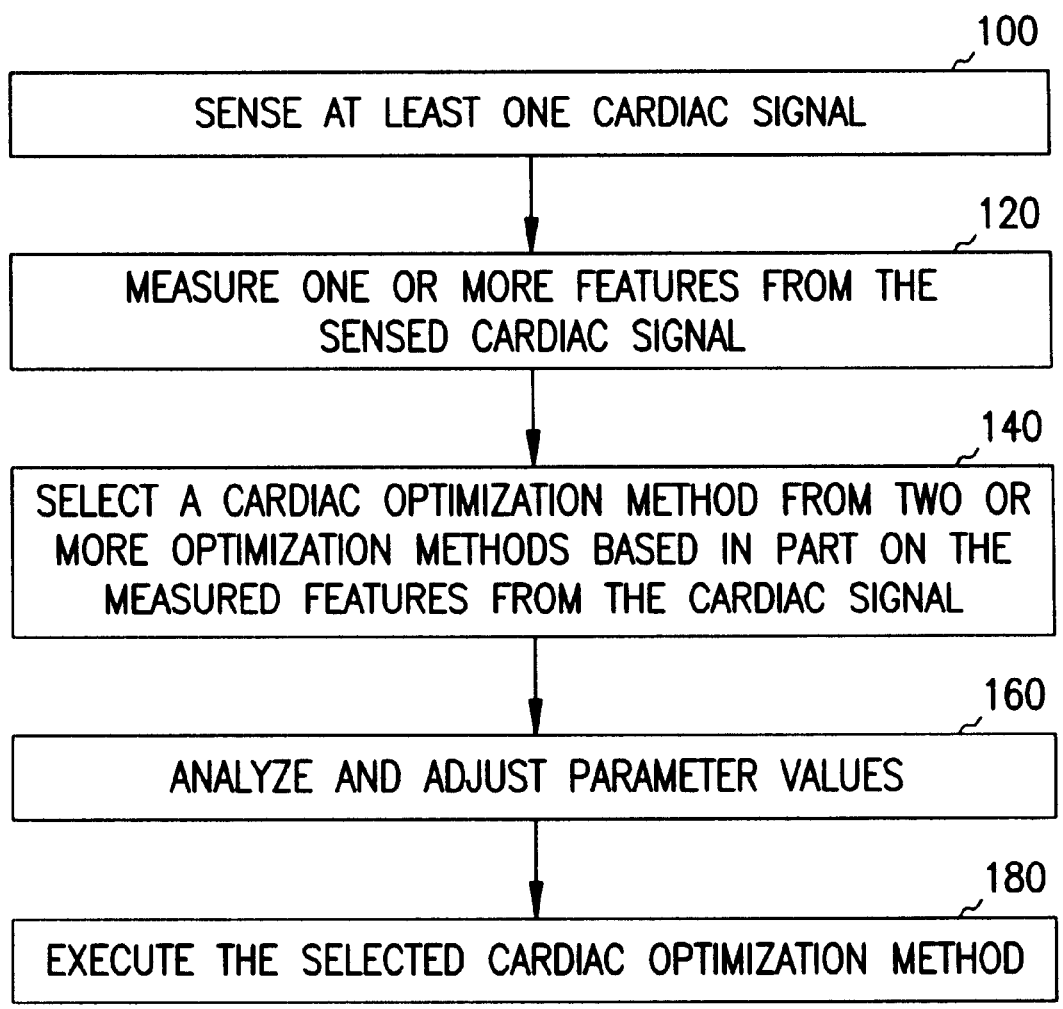
FIG. 1 is a flowchart showing one embodiment of the present subject matter.

In the following detailed description, references are made to the accompanying drawings that illustrate specific embodiments in which the invention may be practiced. Electrical, mechanical, programmatic and structural changes may be made to the embodiments without departing from the spirit and scope of the present invention. The following detailed description is, therefore, not to be taken in a limiting sense and the scope of the present invention is defined by the appended claims and their equivalents.

Advances in implantable pulse generators have lead to devices that contain multiple optimization algorithms for providing pacing and defibrillation pulses. Many of these optimization algorithms have improved resynchronization parameter values that are set automatically based on information sensed or derived from the patient. Examples of such optimization algorithms include pulse pressure optimization (PPO) algorithms that determine improved settings based on candidate therapy-induced changes in heart rate and attempt to improve pulse pressure, maximum pressure versus time algorithms (Max dP/dt algorithms) that determine settings by measuring intrinsic atrio-ventricular (AV) conduction times and attempt to improve the left ventricular contractile function. Other examples of optimization algorithms exist.

One example of an optimization algorithm is U.S. Pat. No. 5,800,471 entitled "Method for Optimizing Cardiac Performance by Determining the Optimal Pacing Mode-AV Delay from the Transient Heart Rate Signal for Use in CHF, Brady, and Tachy/Brady Therapy Devices" (hereinafter "the '471 patent") that is hereby incorporated into the present application in its entirety. The '471 patent describes a cardiac rhythm management device that includes a dual chamber pacemaker especially designed for treating congestive heart failure. The device incorporates a programmed microcontroller that is operative to adjust the pacing mode-AV delay of the pacemaker so as to achieve improved hemodynamic performance. Atrial cycle lengths measured during transient time intervals immediately following a change in the mode-AV delay configuration are signal processed and a determination is then made as to which particular configuration yields improved cardiac performance.

An additional example of an optimization algorithm is U.S. Pat. No. 6,144,880 entitled "Cardiac Pacing Using Adjustable Atrio-Ventricular Delays" (hereinafter "the '880 patent") that is hereby incorporated into the present application in its entirety. The '880 patent is an example of maximum pressure versus time algorithms (Max dP/dt algorithms) that determine settings by measuring intrinsic atrio-ventricular (AV) conduction times and attempt to improve the left ventricular contractile function. The '880 patent provides a pacing system for providing optimal hemodynamic cardiac function for parameters such as contractility (peak left ventricle pressure change during systole or LV+dP/dt), or stroke volume (aortic pulse pressure) using calculated atrio-ventricular delays for optimal timing of a ventricular pacing pulse. The '880 patent describes multiple ways to provide optimized timing for ventricular pacing by determining certain intrinsic electrical or mechanical events in the atria or ventricles that have a predictable timing relationship to the delivery of optimally timed ventricular pacing that maximizes ventricular performance. This relationship allows for a prediction of an atrio-ventricular delay used in delivery of a ventricular pacing pulse relative to a sensed electrical P-wave of the atrium to establish the optimal pacing timing.

One issue with implantable pulse generator systems that have multiple optimization algorithms is how to select the most appropriate method for the patient from the optimization algorithms. Many times, this selection is done by the physician at the time of implanting the device or during a follow-up visit with the patient. This selection process is often accomplished based on limited technical and patient specific information recorded and stored in the device. The present subject matter provides a method and a system for automatically presenting the most appropriate optimization algorithm from multiple optimization algorithms at the time of therapy programming.

The present subject matter provides the following important steps and considerations. First, pertinent information is collected from the patient. This information includes, but is not limited to patient data stored in their implantable device, such as the position of one or more implanted leads (e.g., position adjacent the mid-lateral wall of the left ventricle and/or the mid-septum of the right ventricle), the chamber, or chambers, where a lead is permanently implanted (in right ventricle, adjacent a left ventricle or both right and left ventricles). In one embodiment, the position of the implanted lead(s) and where the leads are implanted are acquired from the patient data. In another embodiment, the position of the implanted lead(s) and where the leads are implanted are determined by analyzing the electrogram and timing of electrical signals recorded on the various leads to predict their positions based on calculated conduction times and cardiac impulse signal morphology. The information further includes current device settings such as current lower rate limit, AV-delay values, LV-offset values (when pacing in right and left ventricle, where the LV-offset value is the time between when the right ventricle pacing pulse is delivered to the time the pacing pulse to the left ventricle is delivered), rate responsive parameters, minute ventilation data and conduction pattern data recorded from surface ECG or intracardiac electrograms (e.g., intraventricular timing, timing of the sensed QRS-complex and the duration interval of sensed QRS complexes). This information is entered by the physician, retrieved from previously stored data in the implantable pulse generator, or recorded automatically from the patient by sensing from the pulse generator or the external programmer.

Second, the most appropriate optimization method is automatically selected based on the patient information. In one embodiment, this is done through the use of a decision tree algorithm executed in either the implantable pulse generator, under the control of a medical device programmer, or executed in the medical device programmer itself. Third, once the optimization method is selected the program parameters are selected, adjusted and the program is executed in the implantable pulse generator or programmer. Examples of the optimization methods include, but are not limited to, PPO algorithms and Max dP/dt algorithms, and other optimization methods that are used to maintain and/or improve cardiac function and are considered to be useful with the present subject matter.

Finally, the optimization results provide a value, or values, for one or more parameters of the optimization method. For example, in the case of the PPO algorithm, a determination and suggestion as to which chambers to pace and AV-delay would be made through the testing process of the algorithm. In addition, the Max dP/dt algorithm would go through multiple parameters and suggest settings for providing the most desirable output. This information is combined with all, or some, of the patient information to provide final parameter settings or recommendations, or to adjust and re-execute the optimization method, or to select and execute a new method, as necessary. The parameter settings allow for improvements in cardiac function, which include, but are not limited to, efficiency of the heart (relation between output and how much energy is expended per heart beat), maximum output of the heart, improved average work produced, and improved peak work done by the heart.

In the present subject matter, various information is measured either by a medical device programmer, or input by a physician. In one embodiment, this information includes the measurement of a cardiac depolarization complex (i.e., QRS complex). This measurement is done either by the physician, automatically by the medical device programmer or the pulse generator. The QRS complex can be measured from a surface ECG recording made by the physician with an external electrocardiographic machine or by the programmer automatically when attached to the patient surface ECG leads. Also, the equivalent of a QRS complex can be measured from implanted lead electrocardiogram signals by the pulse generator or by the programmer from telemetered pulse generator electrogram signals. Based on a selection as to which improved resynchronization parameter values are desired, the present subject matter determines which algorithm needs to be executed. As previously discussed, examples of such optimization algorithms include pulse pressure optimization (PPO) algorithms that determine settings to improve pulse pressure based on changes in heart rate induced by candidate therapies, and maximum pressure versus time algorithms (Max dP/dt algorithms) that determine settings to improve the left ventricular contractile function by measuring intrinsic atrioventricular (AV) conduction times. The cardiac function of the patient is then managed by controlling the pulse generator parameters that control, for example but not limited to, average cardiac output, maximum cardiac output and/or energy efficiency.

The present subject matter can be implemented in either an implantable medical device, such as an implantable pulse generator, or in an external medical device programmer. It can be used at patient follow-ups in the clinic to assist in the optimal programming of the device, or it can be executed automatically in the implanted device when the patient is outside the clinic, as part of an ambulatory, automatic optimization system.

FIG. 1 shows one embodiment of a method according to the present subject matter. At 100, at least one cardiac signal is sensed from a heart. In one embodiment, the cardiac signal is sensed from a right ventricle. In an additional embodiment, the cardiac signal is sensed from a left ventricle. Alternatively, the cardiac signal is a surface ECG sensed through the use of a medical device programmer that is adapted to sense and receive a surface ECG. The types of cardiac signals sensed from the right or left ventricles include unipolar signals or bipolar signals, where the signals are either far field (morphology) or near field (rate).

At 120, one or more features are measured from the sensed cardiac signal. In one embodiment, the features measured from the cardiac signal include, but are not limited to, a duration interval of a QRS complex. In addition, the features include, but are not limited to, information derived from two or more cardiac signals. For example, cardiac signals are sensed from both the right and left ventricles, where a timing delay between the contraction in one of the left or right ventricle and the right or left ventricle, respectively, is taken as the measured feature. In an alternative embodiment, the one or more features could also include blood pressure measurements take from the arterial side of the vasculature, for example with a finger plethysmography sensor. Alternatively, the features could include information related to blood chemistry (e.g., concentrations and/or the presence of specific chemical compounds in the blood). This type of information is also useful in determining the type of optimization method to suggest.

At 140, a cardiac optimization method is then selected from two or more cardiac optimization methods based in part on the measured features from the cardiac signal. In one embodiment, the selection of the cardiac optimization method is based on programmed criteria that provide a hierarchy of the cardiac optimization methods, where given specific features measured from the cardiac signal, or signals, one or more cardiac optimization methods are suggested over one or more other cardiac optimization methods. For example, given the features measured from a patient's cardiac signal, optimizing the AV-delay may take precedence over optimizing which ventricular chamber should be paced or what value to set for an LV-offset. At 160, parameters that are to be used by the selected cardiac optimization method are analyzed to determine whether their values would be within acceptable ranges for programming the implantable pulse generator. Based on this analysis, various recommendations are made with respect to programming the pulse generator. For example, when the parameters fall outside of the acceptable value ranges for the pulse generator, the execution of the optimization method is discontinued and no recommendation is made. Alternatively, adjustments to the parameter values are made, and/or suggested, so as to place the parameter values back within acceptable ranges. Finally, adjustments are made to the remaining portion of the optimization method to only use combinations of the parameters that are within the acceptable range. At 180, the selected cardiac optimization method is then executed.

Figure 2:
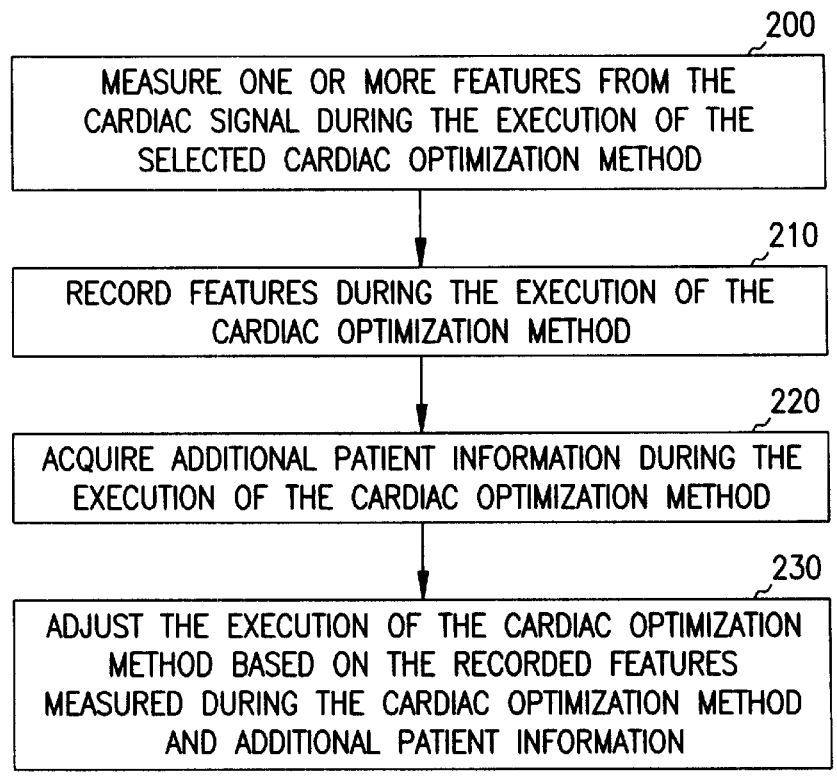
FIG. 2 is a flowchart showing one embodiment of the present subject matter.

FIG. 2 shows an additional embodiment of a method according to the present subject matter. In one embodiment, the subject matter shown in FIG. 2 allows for features measured from the cardiac signal during the optimization method to be combined with additional patient information to allow for adjustments to be made to the operation of the cardiac optimization method. In one respect, the sensed features and patient information is fed back into the operation of the cardiac optimization method to allow for patient specific adjustments to be made to the operation of the cardiac optimization method.

At 200, one or more features are measured from a cardiac signal during the execution of the selected cardiac optimization method. In one embodiment, the one or more features are the features measured and used in identifying which cardiac optimization method to execute, as previously described. The one or more features are then recorded at 210 during the execution of the cardiac optimization method. In addition to recording the features, additional patient information is acquired at 220 during the execution of the cardiac optimization method. In one embodiment, the additional patient information includes, but is not limited to, patient data stored within the implantable device, such as the location of leads implanted in the patient's heart and the number and type of electrodes located on the leads, patient medical history, current device settings, event counters and histograms, and conduction pattern data, such as QRS-complex duration interval. Other types of additional patient information are also possible.

At 230, the recorded features measured during the cardiac optimization method, additional patient information and device parameter settings are used to adjust the execution of the cardiac optimization method. In one embodiment, adjusting the optimization method includes selecting and setting final parameter settings for the cardiac optimization method based on both the additional patient information and the recorded feature measurements. The final parameter settings that result from the features measured during the optimization could result in recommended parameters that may not be acceptable for programming of the implantable pulse generator. One example of this is that the combination of recommended AV delay and LV offset parameters could place the lagging ventricular pace outside of the range that is generally accepted. If this is the case, there are three multiple options available as how to adjust the execution of the optimization method. Three options are discussed here, but there are other methods available that are not discussed here. The first method is to discontinue the execution of the optimization thus providing no recommendation. The second is to adjust one or more of the parameters to place possible recommendations back within the range that is generally accepted prior to continuing the cardiac optimization method. The adjustment of the parameters could be automatic, or based upon input from the user. The third is to modify the remaining portion of the optimization method to only use combinations of the parameters that are within the acceptable range.

In an additional embodiment, the final parameter settings are used in subsequent determinations of parameter values for a different optimization method or other programmable feature of an implantable pulse generator. So, for example, an optimization method and parameter settings are determined for an AV-delay to use with the patient. Once this is determined, the parameter settings used in determining the AV-delay are used in the system to then determined an LV-offset value. Once the LV-offset value is determined, a third cardiac optimization method can then be used to determine a set of third parameter values to use in conjunction with the parameter values of the previous two cardiac optimization methods. In one embodiment, this type of serial determination of parameter values has a hierarchy of items to address and step through sequentially to determine each one and see how each one changes with respect to this value just determined.

In an alternative embodiment, additional adjustments are made to the cardiac optimization method based on the measured features and the patient information. For example, a particular range of values for a cardiac optimization method might be suggested, where the range of values is selected to present the values most likely to improve the patient's heart function, thereby saving the physician time in programming the implantable pulse generator. In an additional embodiment, the feature measurements and the additional patient information is used to trigger a re-execution of the cardiac optimization method. Alternatively, information from the feature measurements and the additional patient information is used to select and execute a second cardiac optimization method from the multiple cardiac optimization methods.

Figure 3:
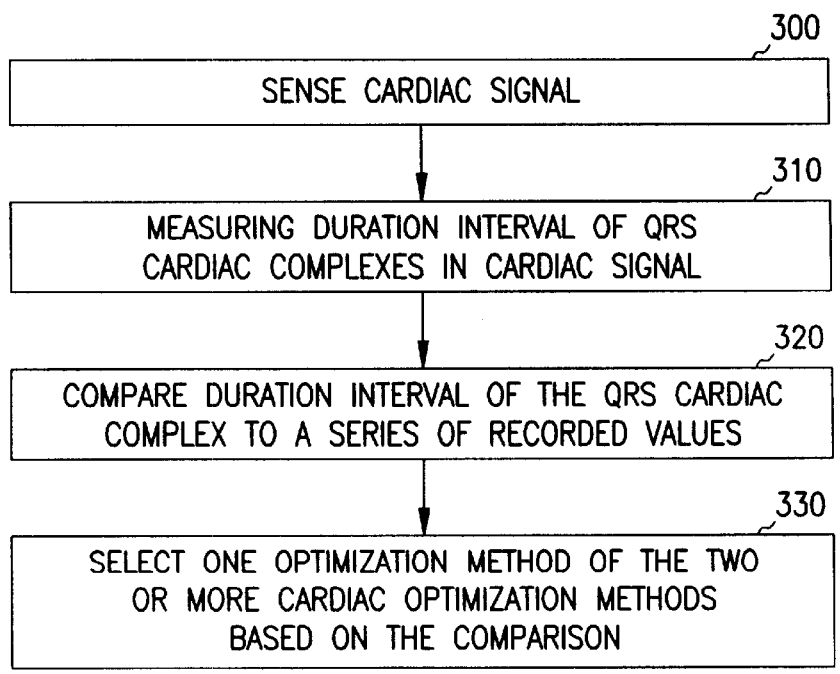
FIG. 3 is a flowchart showing one embodiment of the present subject matter.

FIG. 3 shows an additional embodiment of the present subject matter. As previously discussed, a cardiac signal is sensed at 300. At 310, one or more features are measured from the sensed cardiac signal, where in the present embodiment the measured feature is a duration interval of a QRS cardiac complex. At 320, the duration interval for the QRS cardiac complex is then compared to a series of recorded values. In one embodiment, this comparison results in the duration interval of the QRS cardiac complex being classified as having either a short, a medium or a long duration interval. For the present subject matter, the duration intervals of the QRS cardiac complexes are measured in milliseconds, where a short duration interval for the QRS cardiac complex is less than or equal to 150 milliseconds, a medium duration interval is greater than 150 milliseconds and less than or equal to 160 milliseconds, and a long duration interval is greater than 160 milliseconds.

In one embodiment, the QRS duration is measured at each follow-up visit of the patient. One reason for this is because presently there is insufficient information about how the QRS duration changes with chronic pacing therapy. In one embodiment, the QRS duration is measured from the patient through the use of a 12 lead ECG, where the QRS duration is measured from any of the 12 leads. In one example, the QRS duration is taken from the lead having the maximum QRS duration. In an alternative embodiment, the QRS duration is measured from cardiac signals sensed from leads II, VI and V6. Regardless of the lead, the QRS duration can be measured manually on a paper strip chart recording at a rate of 50 mm/second using standard practice for determining the start and end of the QRS complex. In an alternative embodiment, the duration interval of the QRS complex is measured automatically by the medical device programmer as the cardiac signals are sensed from the surface ECG signal. Alternatively, the duration interval of the QRS complex is measured automatically by the medical device programmer once the medical device programmer downloads stored cardiac signals or telemetered real-time cardiac signals from the implantable medical device. The duration interval of the QRS complex is then compare to the series of recorded values to classify the complex. Based on the classification of the duration intervals of the QRS cardiac complexes at 320, a decision is made at 330 as to which of the two or more cardiac optimization methods will be selected for use.

Figure 4:
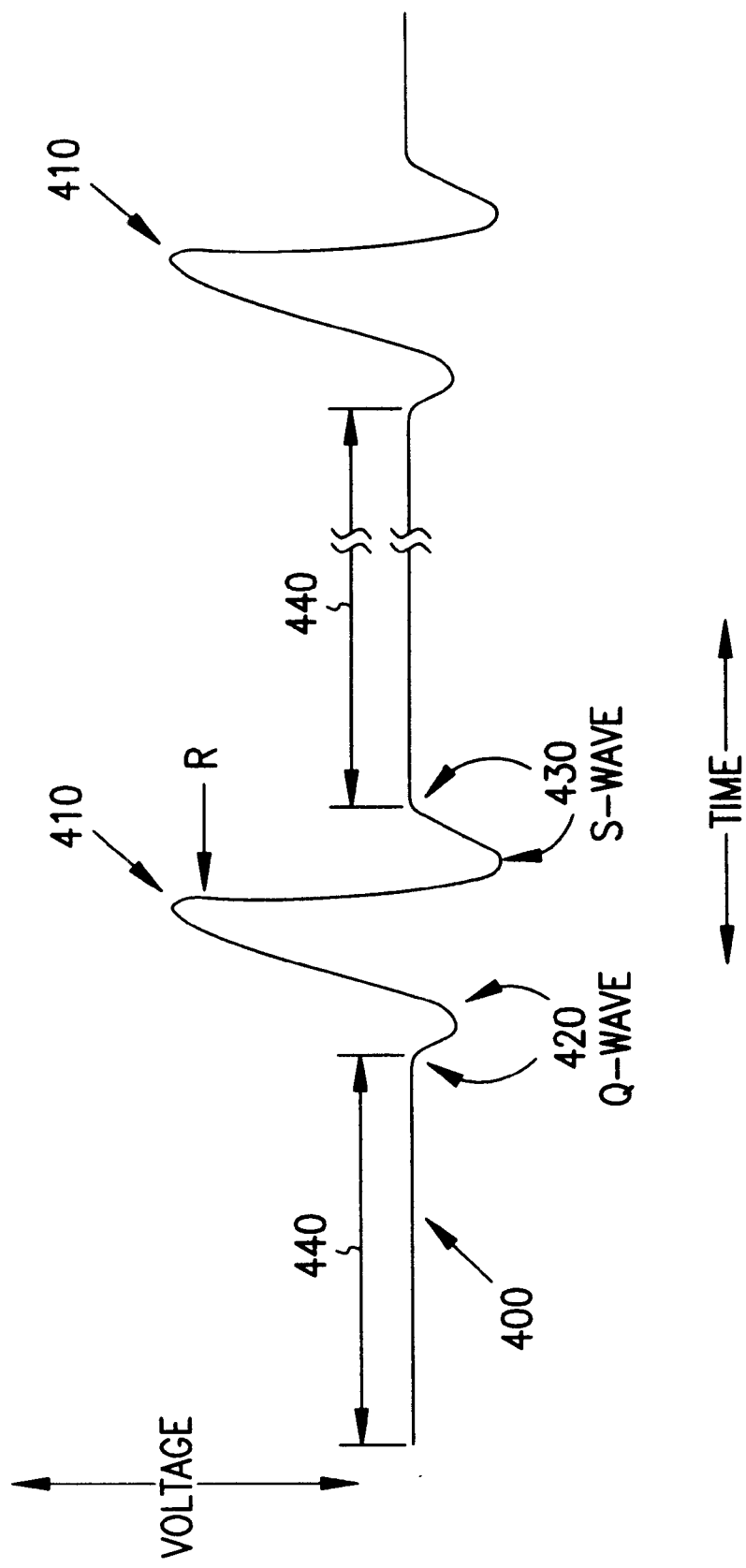
FIG. 4 is an illustration of a cardiac signal according to the present subject matter.

FIG. 4 shows one example of a sensed cardiac signal 400. In one embodiment, the cardiac signal 400 is sensed from a surface ECG. Alternatively, the cardiac signal 400 is measured as a far field signal from two or more electrodes implanted in or around the heart. The sensed cardiac signal 400 includes examples of a QRS cardiac complex 410. The QRS cardiac complex 410 is detected in the cardiac signal 400 as the heart goes through the cardiac cycle, and represents the depolarization phase for the ventricles of the heart.

In one embodiment, the duration of the sensed QRS complex 410 is measured from the beginning of the Q-wave 420 to the end of the S-wave 430, where the beginning of the Q-wave 420 is taken as a deflection from a base line 440 for the start of the Q-wave 420, to the return of the cardiac signal to the base line 440 at the end of the S-wave 430.

In an alternative embodiment, the duration interval of the QRS complex is measured from portions of the QRS complex sensed in two or more cardiac signals. For example, when a first cardiac signal is sensed from a right ventricle and a second cardiac signal is sensed from a left ventricular location, the duration of the QRS complex is determined by the difference of the start of the Q-wave in the first cardiac signal to the end of the S-wave in the second cardiac signal. Alternatively, the duration of the QRS complex is determined by the difference of the start of the Q-wave in the second cardiac signal to the end of the S-wave in the first cardiac signal. Other methods are possible for determining and measuring the duration interval of the QRS cardiac complex and are considered within the scope of the present subject matter.

Figure 5:
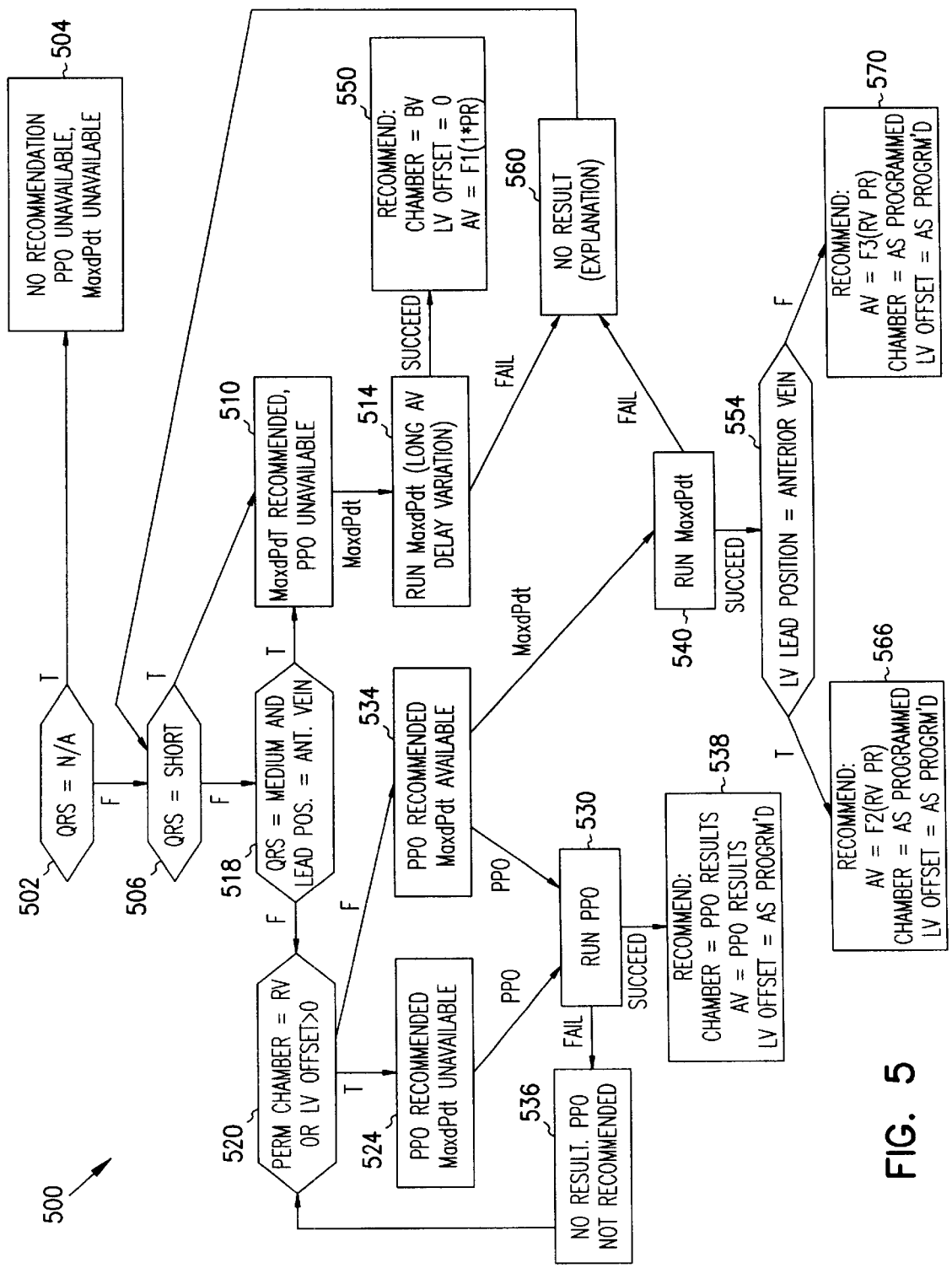
FIG. 5 is a decision tree flowchart showing one embodiment of the present subject matter.

FIG. 5 shows one embodiment of a method 500 according to the present subject matter. The method 500 shows an embodiment of a decision tree for providing a suggested optimization algorithm from among multiple optimization algorithms. As previously discussed, the decision as to which optimization algorithm is selected among the multiple optimization algorithms is based on information that is collected from the patient. This information includes, but is not limited to data stored in their implantable device or supplied by the user, such as the location of one or more implanted leads, conduction disease or disorder (e.g., left bundle branch block, ischemic dilated cardiomyopathy), current device settings, such as lower rate limit, AV-delays, LV-offsets, rate responsive parameters, minute ventilation data, and conduction pattern data (e.g., intraventricular timing, interventricular timing, atrio-ventricular timing, timing of the sensed QRS-complex and the duration interval of sensed QRS complexes). Based on the information, the method 500 allows for optimization methods and programmable values to be suggested for treating the patient. The suggested method can then be implemented in the patient's implantable pulse generator.

The embodiment of FIG. 5 shows a decision between the use of the pulse pressure optimization (PPO) algorithm that determines improved settings based on candidate therapy-induced changes in heart rate and attempts to improve pulse pressure, and the maximum pressure versus time algorithm (Max dP/dt algorithm) that determines settings by measuring intrinsic atrio-ventricular (AV) conduction times and attempts to improve the left ventricular contractile function. The embodiment of FIG. 5, however, is only one example of the decision tree and other decision tree structures that use different and/or additional algorithms are possible and considered within the scope of the present subject matter. In the method 500, a decision between use of the PPO algorithm or the Max dP/dt algorithm is made based in part on the duration interval of the QRS complex measured from the patient. At 502, the duration interval of the patient's QRS complex is measured. In one embodiment, neither feature (PPO or Max dP/dt) is available unless the duration interval of the patient's QRS complex has been measured. One reason for this restriction is due to a safety risk of returning a harmful setting if the method 500 is performed on QRS duration intervals that have not been recently measured from the patient.

As previously mentioned, the PPO algorithm determines improved settings based on therapy-induced changes in heart rate and attempts to improve pulse pressure. The PPO algorithm makes use of a dual chamber pacemaker especially designed for treating congestive heart failure. The device incorporates a programmed microcontroller that is operative to adjust the pacing mode-AV delay of the pacemaker so as to achieve improved hemodynamic performance. Atrial cycle lengths measured during transient time intervals immediately following a change in the mode-AV delay are signal processed and a determination is then made as to which particular configuration yields improved performance.

The Max dP/dt algorithm determines settings by measuring intrinsic atrio-ventricular (AV) conduction times and attempts to improve the left ventricular contractile function. The device provides a pacing system for providing optimal hemodynamic cardiac function for parameters such as contractility (peak left ventricle pressure change during systole or LV+dP/dt), or stroke volume (aortic pulse pressure) using calculated atrio-ventricular delays for optimal timing of a ventricular pacing pulse. The Max dP/dt algorithm makes use of multiple ways to provide optimized timing for ventricular pacing by determining certain intrinsic electrical or mechanical events in the atria or ventricles that have a predictable timing relationship to the delivery of optimally timed ventricular pacing that maximizes ventricular performance. This relationship allows for a prediction of an atrio-ventricular delay used in delivery of a ventricular pacing pulse relative to a sensed electrical P-wave of the atrium to establish the optimal pacing timing.

At 502, the duration interval of the patient's QRS complex is measured. In one embodiment, one representative QRS complex is measured and used. Alternatively, an average or median duration interval for two or more QRS complexes is used. When the duration interval of the QRS complex cannot be measured, the method 500 proceeds to 504, where a display that no recommendation as to either algorithm is made and that both algorithms are not available for use with the implantable pulse generator. When the duration interval of the QRS complex is measured at 502, the method 500 then proceeds to 506. At 506, the QRS cardiac complex is classified as either having a short duration interval or not. In one embodiment, a short duration interval is as described above. When the QRS cardiac complex is classified as a short duration, the method 500 proceeds to 510, where the Max dP/dt algorithm is recommended for use in the pulse generator and the PPO algorithm is made unavailable for use in the pulse generator. After 510, the method 500 proceeds to 514 where determinations for the Max dP/dt algorithm are made and values for use with the Max dP/dt algorithm are made. A more complete discussion of 514 is presented below.

At 506, when the QRS complex is classified as not having a short duration interval, the method 500 proceeds to 518. At 518, the QRS cardiac complex is classified as either having a medium duration interval, as previously discussed, or not, and whether the patient has a cardiac lead located within the anterior cardiac vein. When these two situations are true, the method 500 proceeds to 510 and then to 514, as discussed. However, when either of these two situations is false, the method 500 proceeds to 520. At 520, the system tests to determine whether the right ventricle is the permanently programmed chamber pulse generator parameter setting or whether a value for an LV offset is greater than zero (0). For this latter situation, the system is adapted to provide biventricular pacing, where ventricular pacing pulses are delivered initially to the right ventricle and then to the left ventricle, or vice versa, where the two pacing pulses are offset by the LV offset value.

When either of these conditions is true, the method 500 proceeds to 524. At 524, the PPO algorithm is recommended for use and the Max dP/dt algorithm is made unavailable for use. Different functions for the Max dP/dt algorithm are used only to set the AV delay when biventricular (i.e., both left and right ventricular (BV)) or left ventricular (LV) pacing is indicated by independent means and BV or LV is the permanently programmed chamber and LV offset is not positive. Each of the functions for the Max dP/dt algorithm are used under different cardiac conditions depending upon the location and number of the cardiac electrodes positioned in and around the heart.

The PPO algorithm is then executed at 530 to determine if the algorithm will fail or succeed. In one embodiment, success is when the PPO algorithm executes correctly to completion and returns a valid result, and failure is when the PPO algorithm is unable to complete its execution or returns an error result. In one embodiment, the system cancels the PPO algorithm and restores the device to its permanent mode parameter settings and operation if any of the following conditions occur. First, if the system cannot determine the patient's intrinsic AV delay within the maximum time limit allowed. Second, the PPO algorithm extends beyond the maximum total cardiac cycles allowed. Third, when valid PPO measurements are collected for less than 3 out of 5 trials of any configuration of pacing chambers and AV delay. A trial of a configuration is defined as 5 intrinsic beats plus 5 beats paced in the configuration plus 10 intrinsic beats constituting a washout period. A transient change in valid PPO measurements resulting from the paced beats, compared to the valid PPO measurements resulting from the intrinsic beats that precede the paced beats, provides an indication of the effectiveness of the paced beats compared to the effectiveness of intrinsic beats. To avoid inaccuracies due to noise, randomization and averaging techniques are used to extract data from the repeated trials of each configuration. The particular configuration that results in the largest increase in valid PPO measurements is then utilized in an attempt to optimize the pulse pressure performance of the patient's heart. A trial is classified as an invalid trial if any of the following conditions occur. If a premature ventricular contraction (PVC) or a premature atrial contraction (PAC) is detected anywhere during the trial, or if noise is detected in atrial or ventricular channels during the pacing period. These invalid trials are immediately retried once in an attempt to make it a valid trial. A valid trial that fails a post-execution outlier test is declared to be an invalid trial. These invalid trials cannot be retried because they are determined post-execution. A washout period precedes any trial or re-trial attempt. A washout period is classified as invalid on the cardiac cycle where a PVC or PAC is detected. An invalid washout period is immediately re-tried for up to the maximum time limit allowed after the first cardiac cycle that initiated the washout.

When the PPO algorithm is indicated to have failed at 530, the method 500 proceeds to 536. At 536, no results for either algorithm are presented to the physician and the PPO algorithm is not recommended. The method then returns to 520, where one or both of the permanent chambers and/or the value for the LV offset could be changed. This would allow the method 500 to proceed to 534, instead of 524. Alternatively, the PPO algorithm is executed at 530 and returns a valid result ("succeed") and the method 500 then proceeds to 538. At 538, the PPO algorithm is used to determine suggested pacing chambers for the patient, along with values for the AV offset. In addition to these suggestions, the PPO algorithm suggests the LV offset be set at the value initially programmed.

At 520, when both situations are not true, however, the method 500 proceeds to 534. At 534, the PPO algorithm is recommended and the Max dP/dt algorithm is made available for use by the physician. In one embodiment, the PPO algorithm is recommended when the optimal pacing chamber is unknown and when the maximum output (pulse pressure or stroke volume) is the desired result. With respect to the availability of the Max dP/dt algorithm, when the physician desires a faster optimization method (e.g., less than 20 minutes) due to limited examination time or the maximum force (LV dP/dt$_{max}$) is the desired result, the Max dP/dt algorithm is recommended to set the AV delay.

From 534, a decision is made to proceed with either the PPO algorithm or the Max dP/dt algorithm. When the PPO algorithm is chosen, the method proceeds to 530. Alternatively, when the Max dP/dt algorithm is chosen at 534, the method 500 proceeds to 540. At 540, determinations for the Max dP/dt algorithm are made and values for use with the Max dP/dt algorithm are determined. In one embodiment, determinations and the values for the Max dP/dt algorithm at 540 are similar to those made at 514. Thus, the following discussion pertains to both 514 and 540.

When the Max dP/dt algorithm is executed at 514 and 540, interval measurements between cardiac events are measured according to the Max dP/dt algorithm. When these values are within a specified range of values that are determined to be acceptable for determining a recommended pacing chamber, or chambers, an LV offset and/or an AV delay value, the method 500 proceeds to 550 from 514, or to 554 from 540. When the values are not within the specified range of values determined to be acceptable for determining a recommended pacing chamber, or chambers, an LV offset and/or an AV delay value, either 514 or 540 proceed to 560. At 560, no results are returned for the recommended pacing chamber, or chambers, the LV offset and/or the AV delay value, and an explanation as to why no results were returned is provided. In addition, suggestions for alternative approaches for arriving at suggested results could be given.

As previously discussed, parameter settings for the optimization algorithm, such as those at 514, 530 or 540, are tested to determine whether they are within acceptable value ranges. When the parameter settings for an optimization algorithm are within the acceptable value ranges (e.g., the algorithm succeeds), recommendations as to the parameter settings are made as shown at 538 550 and 566 or 570. When the parameter settings for the optimization algorithm are not within the acceptable value ranges (e.g., the algorithm fails), adjustments to the parameter settings might be made so that the parameter settings for the optimization algorithm are within the acceptable value ranges. In one embodiment, there are three options available to adjust the testing of the optimization algorithm. The first option is to discontinue the execution of the optimization thus providing no recommendation. In FIG. 5, this option leads to one of 536 or 560. The second option is to adjust one or more of the parameters to place possible recommendations back within an acceptable range prior to continuing the cardiac optimization method. The adjustment of the parameters could be automatic, or based upon input from the user. The third is to modify the remaining portion of the optimization method to use only combinations of the parameters that are within the acceptable range. When one of the latter two options are used, the method succeeds and proceeds to one of 538, 550, 566 or 577.

As a part of the adjustments to the parameter settings that take place in 514, 530 or 540 the present subject matter includes value ranges and rules for which the parameter values are compared and analyzed against. As an initial part of the analysis, a verification is made that the AV delay to the first pacing pulse delivered is in the range of 50 to 250 milliseconds. This is done so that the AV delay is within an acceptable clinical range. A verification is also made that a second pace for the AV delay is always delivered before the intrinsic AV delay and not longer than the maximum programmable AV delay. If this second-pace "out-of-bounds" rule is violated prior to testing the AV delay, the AV delay or the LV offset can be shortened until the second pace is no longer out-of-bounds. Alternatively, the AV delay to be tested can be eliminated from the test or an alternative algorithm can be selected that will not require testing of this AV delay. For example, if PPO is selected but the AV delay to be tested results in an out-of-bounds second pace, the Max dP/dt algorithm may be selected instead. If the second-pace out-of-bounds rule is violated after the optimization algorithm has finished executing, the resulting AV delay or the LV offset can be shortened until the second pace is no longer out-of-bounds or the algorithm can return a "fail" result.

At 554, the method 500 then determines whether the system includes a left ventricular lead and, if so, is the left ventricular lead is located in the anterior vein of the patient's heart. When true, the method 500 proceeds to 566. When false, the method proceeds to 570. In each of 550, 566 and 570, the Max dP/dt algorithm, along with additional algorithms, are used to recommend an AV delay value for pacing in the atrium and the ventricle, which of the ventricular chamber, or chambers, to provide pacing in, and when biventricular pacing is recommended along with a recommended LV offset value.

In one embodiment, for both 514 and 540 the Max dP/dt algorithm is represented by the equation AV=k1* PR+k2−LV offset. The Max dP/dt algorithm includes different k1 and k2 coefficient values for three different functions, F1, F2 and F3, of the Max dP/dt algorithm equation, where each of the functions F1, F2 and F3 are used in 550, 566 and 570, respectively. Each of the equations for the Max dP/dt algorithm are used under different cardiac conditions depending upon the location and number of the cardiac electrodes positioned in and around the heart.

With respect to 550, the function F1 of the Max dP/dt algorithm is a linear function of the PR interval measured from an atrial sense marker to a first ventricular sense marker (1st PR). In one embodiment, the sense markers indicate where the cardiac event was determined to have occurred as the cardiac signal was sensed. In addition, the first ventricular sense marker is taken as the first of either a left ventricular depolarization or a right ventricular depolarization in a biventricular pacing/sensing system.

Function F1 is intended to set the AV delay value just shorter than the shortest intrinsic AV delay. In one embodiment, the shortest AV delay is taken as the PR interval measured from the atrial sense marker to the first ventricular sense marker (1st PR). For function F1, the PR interval is determined from the atrial sense marker to the 1st ventricular sense marker plus a constant offset value "d". The constant offset value d is added to the PR interval to adjust for the difference between the ventricular sense marker and the time of the peak R-wave depolarization that was originally used to derive the coefficients k1 and k2. In one embodiment, the constant offset value "d" is set in a range of 10 to 100 milliseconds. For F1, coefficient k1 is equal to 0.70 and coefficient k2 is equal to zero (0.0). Also in 550, a recommendation for pacing in both the right and left ventricles (biventricular) is made, along with setting the LV offset from the right ventricular pacing pulse to zero (0.0). However, it is also valid to use the AV delay from the F1 Max dP/dt formula with other pacing chambers, such as the right ventricle or the left ventricle, if these are independently selected by the physician.

With respect to 566, the function F2 of the Max dP/dt algorithm is a linear function of the PR interval measured from an atrial sense marker to a right ventricular sense marker (RV PR). In one embodiment, the sense markers indicate where the cardiac event was determined to have occurred as the cardiac signal was sensed. In addition, the right ventricular sense marker is taken as the indicator of the depolarization of the right ventricle. For function F2, the PR interval is determined from the atrial sense marker to the right ventricular sense marker plus the constant offset value "d", as previously described. In one embodiment, coefficient k1 is equal to 0.75 and coefficient k2 is equal to −60 for function F2. Also at 566, a recommendation for pacing in the ventricular chambers as originally programmed and allowing the LV offset to remain as programmed (negative or zero) are recommended for use with the Max dP/dt algorithm.

With respect to 570, the function F3 of the Max dP/dt algorithm is a linear function of the PR interval measured from an atrial sense marker to a right ventricular sense marker (RV PR). In one embodiment, the sense markers indicate where the cardiac event was determined to have occurred as the cardiac signal was sensed. In addition, the right ventricular sense marker is taken as the indicator of the depolarization of the right ventricle. For function F3, the PR interval is determined from the atrial sense marker to the right ventricular sense marker plus the constant offset value "d", as previously described. In one embodiment, coefficient k1 is equal to 0.60 and coefficient k2 is equal to −30 for function F3. Also at 570, a recommendation for pacing in the ventricular chambers as originally programmed and allowing the LV offset to remain as programmed (negative or zero) are recommended for use with the Max dP/dt algorithm.

In one embodiment, the Max dP/dt algorithm of F2 and F3 are not available when the pacing chamber is programmed to only the right ventricle, or is programmed to a biventricular mode with a positive LV offset value (i.e., pacing the right ventricle before the left ventricle). Thus, the F2 and F3 Max dP/dt functions are not valid for these cases. However, these functions likely can be used when biventricular chamber pacing is used and the LV offset is negative. In one embodiment, when biventricular pacing is used with a negative offset, the best AV delay to the left ventricular pace is usually constant regardless of the LV offset. Thus, functionally the LV offset behaves as if it is an RV offset, that is, the best AV delay to pre-excite the left ventricle is constant and improvement in the cardiac function is seen by pacing the right ventricle after the left ventricle rather than simultaneously. This means that the Max dP/dt algorithm functions to return the AV delay that is the best time to pace the left ventricle, and not the right ventricle. Therefore, to adjust for right ventricular timing, the Max dP/dt algorithms are modified to add the LV offset (subtract the negative offset) to the computed AV delay so the AV delay represents the right ventricular pace delay and the LV offset paces the left ventricle at the correct time.

Figure 6:
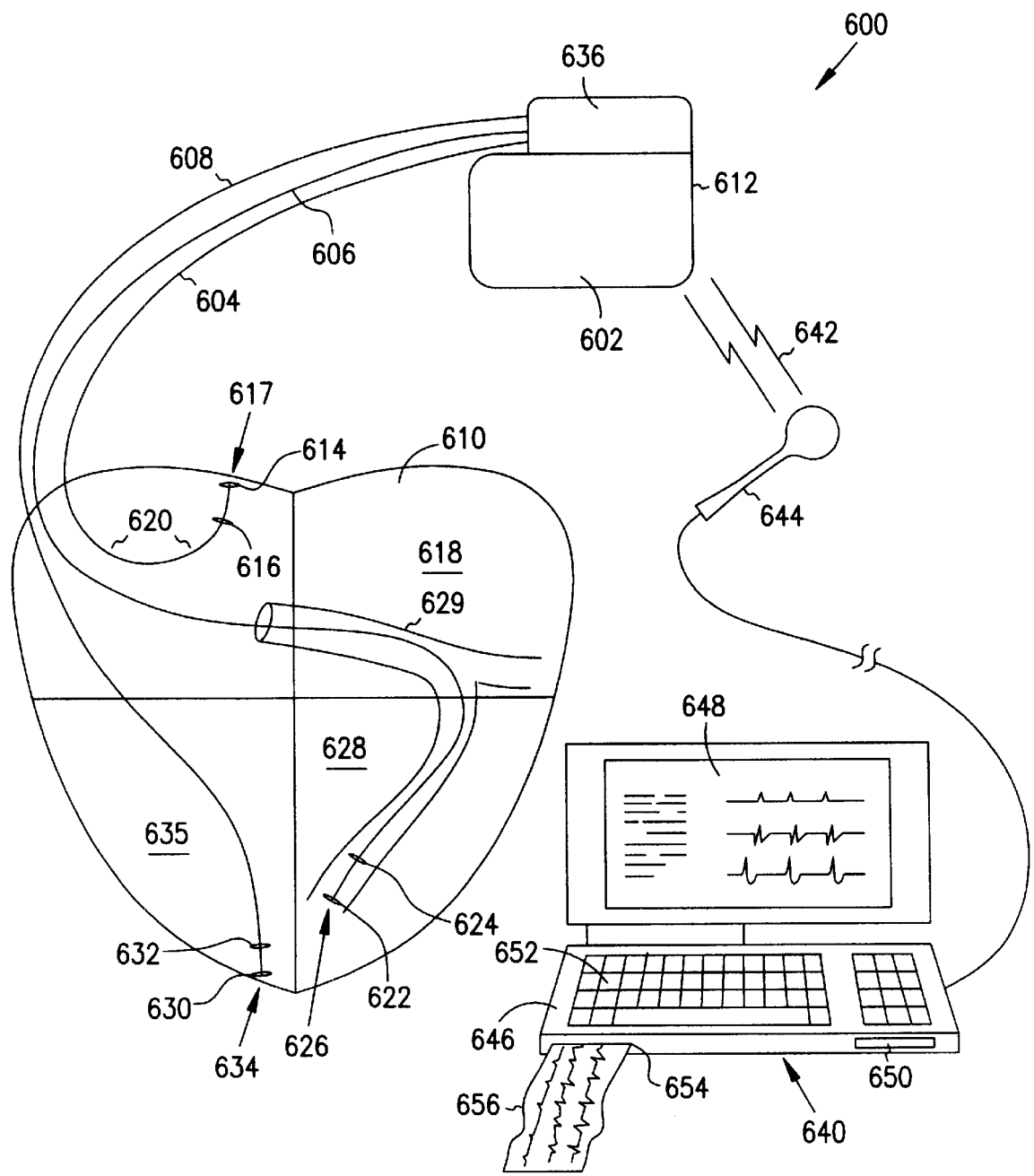
FIG. 6 is a schematic drawing illustrating one embodiment of a system of medical device programmer and an implantable pulse generator coupled by leads to a heart.

FIG. 6 is a schematic drawing illustrating, by way of example, but not by way of limitation, one embodiment of a system 600 that includes an implantable pulse generator 602 and a medical device programmer 640. The implantable pulse generator 602 is shown coupled by leads 604, 606 and 608 to a heart 610. In the present embodiment, the pulse generator 602 provides for biventricular therapy to coordinate right ventricular and left ventricular contractions, such as for congestive heart failure patients. The pulse generator 602 also contains control circuitry within housing 612 that receives and analyzes cardiac signals sensed and provides energy pulses with the leads 604, 606 and 608 under certain predetermined conditions.

In one embodiment, lead 604 is shown with a first atrial sensing/pacing electrode 614 and a second atrial sensing/pacing electrode 616. In one embodiment, the first atrial sensing/pacing electrode 614 is a tip electrode located at a distal end 617 of lead 604. Alternatively, first atrial sensing/pacing electrode 614 is a ring electrode that partially or completely encircles the lead body of lead 604 at a position proximal to the distal end 617. In an additional embodiment, the second atrial sensing/pacing electrode 616 is a ring electrode that partially or completely encircles the lead body of lead 604 and is positioned proximal to both the distal end 617 and the first atrial sensing/pacing electrode 614. Lead 604 is adapted to be implanted in a supraventricular region 618 of the heart 610, where the body of lead 604 includes a J-curve 620 near the proximal end 616 to allow the distal end 617 to be implanted into the endocardium of the heart 610. In one embodiment, the distal end 617 of lead 604 is implanted in the right atrial appendage to allow for a cardiac signal to be sensed from the supraventricular region of the heart. In another embodiment, the distal end 617 is implanted at the right atrial septum between Koch's triangle and Bachmann's bundle. In the embodiment shown in FIG. 6, the cardiac signal is sensed from and for electrical energy pulses (e.g., pacing level pulses) to be delivered to the right atrium of the heart 610. In one embodiment, the cardiac signal sensed with lead 604 is a bipolar cardiac signal sensed between the first and second atrial sensing/pacing electrode 614 and 616. Alternatively, a unipolar cardiac signal is sensed between either the first or second atrial sensing/pacing electrode 614 or 616 and the housing 612.

In one embodiment, lead 606 is shown with a first left ventricular sensing/pacing electrode 622 and a second left ventricular sensing/pacing electrode 624. In one embodiment, the first left ventricular sensing/pacing electrode 622 is a tip electrode located at a distal end 626 of lead 606. Alternatively, first left ventricular sensing/pacing electrode 622 is a ring electrode that partially or completely encircles the lead body of lead 606 at a position proximal to the distal end 626. In an additional embodiment, the second left ventricular sensing/pacing electrode 624 is a ring electrode that partially or completely encircles the lead body of lead 606 and is positioned proximal to both the distal end 626 and the first left ventricular sensing/pacing electrode 622. In an alternative embodiment, lead 608 can include only the first left ventricular sensing/pacing electrode 622, without the second left ventricular sensing/pacing electrode 624.

Lead 606 is adapted to be implanted into the heart 610 with the distal portion of the lead 606 positioned in an epicardial location adjacent the left ventricle 628. In one embodiment, the distal end 626 of lead 606 is inserted through the coronary sinus vein 629, thence through the great cardiac vein and into a lateral branch of the left ventricular coronary vasculature to position the first and second left ventricular sensing/pacing electrodes 622 and 624 adjacent the lateral wall of the left ventricle 628 to allow for a cardiac signal to be sensed from and for electrical energy pulses (e.g. pacing level pulses) to be delivered to the left ventricular region of the heart. In one embodiment, the cardiac signal sensed with lead 606 is a bipolar cardiac signal sensed between the first and second left ventricular sensing/pacing electrode 622 and 624. Alternatively, a unipolar cardiac signal is sensed between either the first or second left ventricular sensing/pacing electrode 622 or 624 and one or more electrodes implanted in the right ventricle. Examples of these right ventricular electrodes are described below in conjunction with lead 608. Alternatively, the housing 612 can be used as the return electrode (anode) with either the first or second left ventricular sensing/pacing electrode 622 or 624.

In one embodiment, lead 608 is shown with a first right ventricular sensing/pacing electrode 630 and a second right ventricular sensing/pacing electrode 632. In one embodiment, the first right ventricular sensing/pacing electrode 630 is a tip electrode located at a distal end 634 of lead 608. Alternatively, first right ventricular sensing/pacing electrode 630 is a ring electrode that partially or completely encircles the lead body of lead 608 at a position proximal to the distal end 634. In an additional embodiment, the second right ventricular sensing/pacing electrode 632 is a ring electrode that partially or completely encircles the lead body of lead 608 and is positioned proximal to both the distal end 634 and the first right ventricular sensing/pacing electrode 630. Lead 608 is adapted to be implanted in a right ventricular region 635 of the heart 610. In one embodiment, the distal end 634 of lead 608 is implanted in the apex of the right ventricle 635 to allow for a cardiac signal to be sensed from and for electrical energy pulses (e.g., pacing level pulses) to be delivered to the right ventricular region of the heart 610. In another embodiment, the distal end 634 of lead 608 is implanted at the right ventricular septum between the right ventricular apex and outflow tract. In one embodiment, the cardiac signal sensed with lead 608 is a bipolar cardiac signal sensed between the first and second right ventricular sensing/pacing electrode 630 and 632. Alternatively, a unipolar cardiac signal is sensed between either the first or second right ventricular sensing/pacing electrode 630 or 632 and the housing 612.

In an additional embodiment, any one of the leads 604, 606 or 608 can include additional electrodes attached to the lead body. Examples include, but are not limited to, the leads further including one or more additional sensing/pacing electrodes and/or one or more defibrillation coil electrodes. In addition, cardiac signals and energy pulses delivered by the electrodes can be delivered in any number of additional ways, including, but not limited to, cardiac signals and energy pulses being delivered between two or more of any combination of sensing/pacing electrodes shown in FIG. 6 or additional electrodes that might be added to the pulse generator 602 of FIG. 6.

Pulse generator 602 further includes components, such as the electronic control circuitry, enclosed in the housing 612. Additional electrodes may be located on the housing 612, may be the housing 612 itself, may be on an insulating header 636, or on other portions of the pulse generator 602, for providing unipolar or bipolar pacing/sensing and/or defibrillation energy in conjunction with the electrodes disposed on or around heart 610. Other forms of electrodes include meshes and patches which may be applied to portions of heart 610 or which may be implanted in other areas of the body to help "steer" electrical currents produced by the generator 602. The present method and apparatus will work in a variety of configurations and with a variety of electrical contacts or "electrodes." The system 600 further includes medical device programmer 640 that provides for wireless communication with the electronic control circuitry within the pulse generator 602. The medical device programmer 640 is adapted to be positioned outside the human body for communication with the pulse generator 602. Communication between the electronic control circuitry within the pulse generator 602 and the medical device programmer 640 occurs over a communication link 642 that is established between programmer 640 and the pulse generator 602 through the use of a telemetry device 644. In one embodiment, the telemetry device 644 is inductively coupled to control circuitry within the medical device programmer 640. In another embodiment, the communication link established between the programmer 640 and the pulse generator 602 is a radio frequency link.

In one embodiment, the medical device programmer 640 includes electronic circuitry within a housing 646, where a graphics display screen 648 is disposed on an upper surface of the housing 646. The programmer 640 further includes a drive 650 for reading and writing instructions used by the electronic circuitry of the programmer 640. The graphics display screen 648 is operatively coupled to the electronic circuitry within the housing 646 and is adapted to provide a visual display of graphics and/or data to the user.

The programmer 640 further includes input devices to the electronic circuitry. For example, the programmer 640 includes a touch-sensitive display screen, such that the user interacts with the electronic circuitry by touching identified regions of the screen with either their finger or with a stylus. In addition, the programmer 640 further includes an alphanumeric key board 652 for providing information, such as programmable values for the implantable medical device, to the electronic circuitry in the medical device 602. FIG. 6 also shows the programmer 640 having a printer 654 which allows for cardiac signals received from the implantable medical device 602 to not only be displayed on the graphics display screen 648, but also to be displayed on a paper printout 656. Adjustments for printer speed and scale of the printed cardiac signals is adjustable through the use of the display screen 648 and the electronic circuitry within the programmer 640.

In one embodiment, the present subject matter is executed using only the electronic control circuitry within medical device programmer 640. Alternatively, the present subject matter is executed using the electronic control circuitry within both the medical device programmer 640 and the implantable medical device 602. In this latter embodiment, the electronics within each of the devices 602 and 640 perform various portions of the algorithm of the present subject matter and the algorithms of the optimization algorithms. In one embodiment, the programmer is used to direct and control the execution of the present subject matter. Thus, most of the subject matter discussed for FIGS. 1–5 is executed in the control circuitry of the medical device programmer, where the programmer uses the pulse generator to retrieve patient specific data from the pulse generator and cardiac signals sensed through the use of the pulse generator. Once the programmer has received this information, the programmer executes a decision tree, such as the example of FIG. 5. Once a decision as to a recommended optimization algorithm, and the parameters to be used, is arrived at, the programmer can then be used to program the pulse generator to perform an optimization test. In one embodiment, the optimization test is used to determine if the parameters determined by the programmer for the optimization algorithm are acceptable and functional in the pulse generator. After the control circuitry of the pulse generator completes the optimization test, the results of the test are returned to the programmer for analysis by the programmer and/or the physician.

Figure 7:
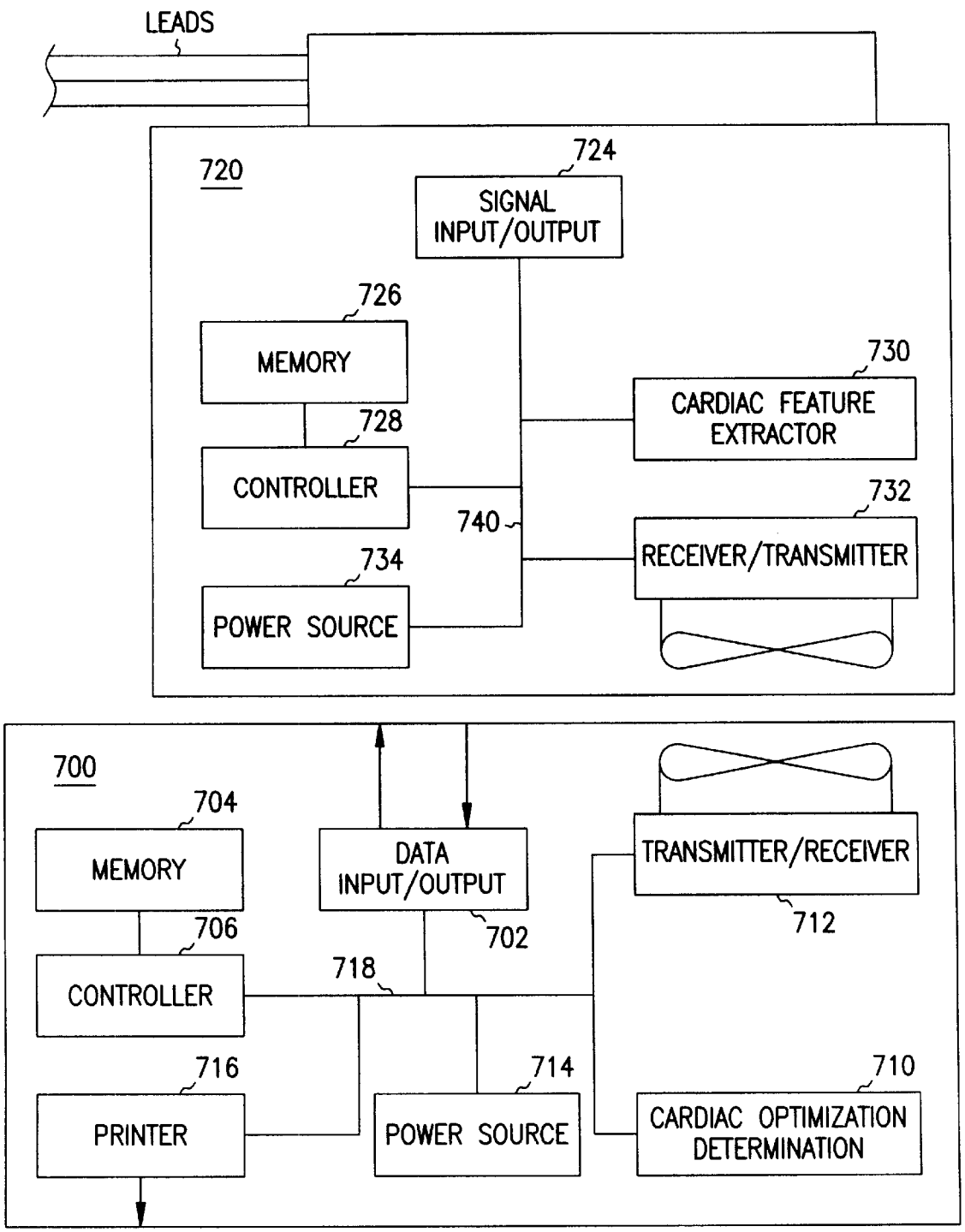
FIG. 7 is a block diagram illustrating one embodiment of control circuitry of the system according to the present subject matter.

FIG. 7 shows one embodiment of the control circuitry for both the medical device programmer 640 and the implantable pulse generator 602 that comprise system 600. In one embodiment, both the implantable pulse generator 602 and the medical device programmer 640 are microprocessor-based devices. In one embodiment, the system 600 includes a cardiac signal feature extractor to measure one or more features from a cardiac signal, a cardiac algorithm optimizer, where the cardiac algorithm optimizer selects a cardiac optimization method from two or more cardiac optimization methods based in part on the measured features from the cardiac signal, and a controller that executes the selected cardiac optimization method. In one embodiment, these components of the system 600 are divided between the implantable pulse generator 602 and the medical device programmer 640 so that both devices are used in executing the methods of the present subject matter. Alternatively, these components of system 600 are included in only one of either the implantable pulse generator 602 or the medical device programmer 640. FIG. 7 shows one embodiment where the components of the system 600 are divided between the implantable pulse generator 602 and the medical device programmer 640.

In one embodiment, the medical device programmer 640 includes programmer control circuitry 700 having data input/output 702, memory 704, controller 706, cardiac algorithm optimizer 710, transmitter/receiver 712, power source 714 and printer 716. The controller communicates with the associated circuitry (e.g., data input/output 702, memory 704, controller 706, cardiac algorithm optimizer 710 and transmitter/receiver 712) via bus 718. In one embodiment, the data input/output 702 includes read/write drives and data transfer between the control circuitry and the keyboard and screen.

In one embodiment, the implantable pulse generator 602 includes pulse generator control circuitry 720 having signal input/output 724, memory 726, controller 728, cardiac signal feature extrator 730, transmitter/receiver 732, and a power source 734. The controller communicates with the associated circuitry (e.g., signal input/output 724, memory 726, controller 728, cardiac signal feature extrator 730 and transmitter/receiver 732) via bus 740. In one embodiment, the signal input/output 724 includes connectors for coupling to the electrodes located on the leads, amplifiers for amplifying cardiac signals sensed with the electrodes and controls for generating and delivering electrical energy pulses to the electrodes. In addition, the transmitter/receiver 732 is adapted to establish a communication link with the transmitter/receiver 712 of the medical device programmer 640 to allow for patient specific information, including cardiac signals sensed from the patient, to be transferred between the two devices.

In the present example, the cardiac signal feature extrator 730 of the implantable pulse generator 602 is used to measure one or more features from a cardiac signal, the cardiac algorithm optimizer of the medical device programmer 640 is used to select a cardiac optimization method from two or more cardiac optimization methods based in part on the measured features from the cardiac signal and the controller 706 of the medical device programmer 640 or the controller 728 of the implantable pulse generator 602 are used to execute the selected cardiac optimization method.

In one embodiment, when the system 700 is used to select a cardiac optimization method, the implantable pulse generator 602 is used to sense one or more cardiac signals from the heart. From the sensed cardiac signals, the programmer 640 is used to identify a cardiac optimization method from two or more methods for use in the pulse generator 602, as previously described. Once the cardiac optimization method is identified it is tested to determine whether the parameter values suggested for use with the optimization method can be used with the pulse generator 602, as previously described. To accomplish this task, the cardiac signal feature extractor 730 measures features from the cardiac signal during the execution of the selected cardiac optimization method, as previously discussed, and records the features measured during the cardiac optimization method. The controller 706 also acquires additional patient information via a transmitter/receiver telemetry link during the cardiac optimization method. The cardiac algorithm optimizer 710 then adjusts the execution of the cardiac optimization method based on the recorded features measured during the cardiac optimization method and the additional patient information.

In one embodiment, the cardiac algorithm optimizer 710 determines parameter values for use with the cardiac optimization method based on the recorded features and the additional patient information. In one embodiment, the cardiac algorithm optimizer 710 analyzes the parameter values to determine whether the values are within acceptable value ranges, where the acceptable value ranges are stored in memory 704. As previously discussed, there are several options in responding to the situation where the parameter values are not within acceptable value ranges. One option is for the programmer 640 to make no recommendation and to discontinue the execution of the optimization method. Alternatively, the cardiac algorithm optimizer 710 adjusts the parameter values to place the parameter values within acceptable value ranges. Finally, the cardiac algorithm optimizer 710 could be used to make adjustments to the remaining portion of the optimization method (e.g., additional parameter values) to only use combinations of the parameters that are within the acceptable range.

As previously discussed, the adjustments to the optimization algorithms occur once an algorithm has been identified based on measured portions of the sensed cardiac signals (e.g., QRS duration), location of the implanted leads, and/or values for an LV offset. FIG. 5 was one such example. In one embodiment, the system 700 is used in making a decision between the use of the pulse pressure optimization (PPO) algorithm and maximum pressure versus time algorithm (Max dP/dt algorithm). As previously discussed, the decision between use of the PPO algorithm or the Max dP/dt algorithm is made based in part on the duration interval of the QRS complex. In one embodiment, the cardiac signal feature extractor 730 measures the duration interval of the QRS cardiac complex in the sensed cardiac signal. The cardiac algorithm optimizer 710 then compares the duration interval to the series of recorded values. The cardiac algorithm optimizer 710 then selects the cardiac optimization method based on the comparison of the duration interval to the series of recorded values, as previously discussed.

In one embodiment, the cardiac algorithm optimizer 710 classifies the duration interval as either a short duration interval or a medium duration interval. In one embodiment, when the duration interval is classified as the short duration interval, the cardiac algorithm optimizer 710 recommends a Max dP/dt algorithm and makes a pulse pressure optimization algorithm unavailable. The cardiac algorithm optimizer 710 then determines values for use with the Max dP/dt algorithm and the controller 706 executes the Max dP/dt algorithm to determine whether the suggested parameter values can be used with the pulse generator 602. In one embodiment, the cardiac signal feature extrator 730 is used to measure intervals between cardiac events, where the cardiac algorithm optimizer 710 determines whether the intervals are within a specified range of values. The cardiac algorithm optimizer 710 then recommends one or more pacing chambers, and an LV offset or an AV delay value when the intervals are within the specified range of values. In one embodiment, the cardiac algorithm optimizer 710 recommends biventricular chamber pacing and the LV offset equal to zero, and calculates the AV delay from the linear function from the PR interval measured from an atrial sense marker to a first ventricular sense marker, as previously discussed. However, when the intervals are not within the specified range of values, the cardiac algorithm optimizer 710 does not recommend one or more pacing chambers and the LV offset or the AV delay value, as previously discussed.

In an additional embodiment, the cardiac algorithm optimizer 710 recommends the Max dP/dt algorithm and makes the pulse pressure optimization algorithm unavailable when the cardiac signal feature extractor 730 determines a cardiac lead is located within the anterior cardiac vein and the duration of the QRS complex is classified as the medium duration interval. In one embodiment, the controller 706 executes the Max dP/dt algorithm when the cardiac lead is located within the anterior cardiac vein using values for the Max dP/dt algorithm determined with the cardiac signal feature extractor 730. As the Max dP/dt algorithm is executed, the cardiac signal feature extractor 730 measures intervals between sensed cardiac events. The cardiac algorithm optimizer 710 then determines whether the intervals are within the specified range of values, as previously discussed. When the intervals are within the specified range of values, the cardiac algorithm optimizer 710 recommends one or more pacing chambers and values for the LV offset and the AV delay. In one embodiment, the cardiac algorithm optimizer 710 recommends biventricular chamber pacing, the LV offset equal to zero and calculates the AV delay from the linear function using the PR interval measured from an atrial sense marker to a first ventricular sense marker, as previously described, when the intervals are within the specified range of values. However, when the intervals are not within the specified range of values, the cardiac algorithm optimizer 710 does not provide recommendations for one or more pacing chambers or values for the LV offset and the AV delay.

In an alternative embodiment, when either a right ventricle is the permanently programmed chamber or the value for an LV offset is greater than zero, then the cardiac algorithm optimizer 710 recommends the PPO algorithm and makes the Max dP/dt algorithm unavailable. The controller 728 then executes the PPO algorithm and determines whether the pulse pressure optimization algorithm fails or succeeds, as previously discussed. If the PPO algorithm fails, then the cardiac algorithm optimizer 710 returns no result and the PPO algorithm is not recommended. However, if the controller 728 determines the PPO algorithm succeeds, then the cardiac algorithm optimizer 710 determines suggested pacing chambers for the patient and determines values for an AV offset from the pulse pressure optimization algorithm, and suggests the LV offset be set at an initially programmed value.

In an alternative embodiment, when either the right ventricle is not the permanently programmed chamber or the value for the LV offset is less than or equal to zero, then the cardiac algorithm optimizer 710 recommends the PPO algorithm. The controller 728 then executes the PPO algorithm and determines whether the PPO algorithm fails or succeeds, as previously discussed. If the PPO algorithm fails, then the cardiac algorithm optimizer 710 returns no result and the PPO algorithm is not recommended. However, if the controller 728 determines the PPO algorithm succeeds, then the cardiac algorithm optimizer 710 determines suggested pacing chambers for the patient and determines values for the AV offset and suggests the LV offset be set at an initially programmed value.

In an additional embodiment, the cardiac algorithm optimizer does not recommend one or more pacing chambers, the LV offset or the AV delay value when the measured intervals between the cardiac events for use with the Max dP/dt algorithm are not within the specified range of values and the left ventricular lead position is in an anterior vein. Alternatively, the cardiac algorithm optimizer 710 recommends one or more pacing chambers and the LV offset to remain as programmed and the AV delay value to be determined from the linear function of the PR interval measured from the atrial sense marker to the right ventricular sense marker when the intervals are within the specified range of values when the left ventricular lead position is in the anterior vein and when the intervals are within the specified range of values, as previously discussed. Finally, the cardiac algorithm optimizer 710 recommends one or more pacing chambers and the LV offset to remain as programmed and the AV delay value to be determined from the linear function of the PR interval measured from the atrial sense marker to the right ventricular sense marker when the left ventricular lead position is not in the anterior vein and when the intervals are within the specified range of values, as previously discussed.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

We claim:

1. A method for setting operating parameters of a cardiac rhythm management device, comprising:
   determining the degree of ventricular asynchrony existing in a patient; and
   selecting between a parameter optimization algorithm that maximizes cardiac output and a parameter optimization algorithm that maximizes myocardial contractility based upon the degree of ventricular asynchrony.

2. The method of claim 1 wherein the degree of ventricular asynchrony is determined by measuring a feature extracted from a cardiac signal.

3. The method of claim 2 wherein the measured feature is the duration interval of a QRS complex.

4. The method of claim 2 wherein the parameter optimization algorithm that maximizes cardiac output is a pulse pressure optimization algorithm.

5. The method of claim 4 wherein the pulse pressure optimization algorithm recommends an optimum AV delay.

6. The method of claim 4 wherein the parameter optimization algorithm that maximizes myocardial contractility recommends an optimum AV delay based upon a measured intrinsic atrio-ventricular conduction delay.

7. The method of claim 6 wherein the pulse pressure optimization algorithm is selected in preference to the myocardial contractility maximizing algorithm when a relatively large degree of ventricular asynchrony exists.

8. The method claim 7 wherein a large degree of ventricular asynchrony is indicated by a QRS duration interval greater than 160 milliseconds.

9. The method of claim 6 wherein the contractility maximizing algorithm is selected when the QRS interval duration is classified as short.

10. The method of claim 9 wherein the contractility maximizing algorithm is selected when the QRS interval duration is classified as medium and a lead of the pulse generator is located in the anterior cardiac vein.

11. The method of claim 10 wherein the pulse pressure optimization algorithm is selected if the QRS interval duration is classified as long.

12. The method of claim 11 wherein the contractility maximizing algorithm, if successful, recommend biventricular pacing with zero offset if the QRS interval duration is classified as short.

13. The method of claim 12 wherein successful execution of the pulse pressure optimization algorithm results in recommendations for chambers to be paced and for the programmed AV delay.

14. The method of claim 13 wherein the pulse pressure optimization algorithm and the contractility maximizing algorithm are both selected if the QRS interval duration is classified as long and neither the right ventricle is the sole paced chamber nor is the LV offset greater than zero.

15. The method of claim 1 wherein the selection of a parameter optimization algorithm is further based upon whether the parameter settings recommended by an algorithm are within acceptable ranges.

16. A system for setting operating parameters of a cardiac rhythm management device, comprising:
    a cardiac algorithm optimizer for determining the degree of ventricular asynchrony existing in a patient and selecting between a parameter optimization algorithm that maximizes cardiac output and a parameter optimization algorithm that maximizes myocardial contractility based upon the degree of ventricular asynchrony; and,
    a controller for executing the selected parameter optimization algorithm.

17. The system of claim 16 wherein the degree of ventricular asynchrony is determined by measuring a feature extracted from a cardiac signal.

18. The system of claim 17 wherein the measured feature is the duration interval of a QRS complex.

19. The system of claim 17 wherein the parameter optimization algorithm that maximizes cardiac output is a pulse pressure optimization algorithm.

20. The system of claim 19 wherein the pulse pressure optimization algorithm recommends an optimum AV delay.

21. The system of claim 19 wherein the parameter optimization algorithm that maximizes myocardial contractility recommends an optimum AV delay based upon a measured intrinsic atrio-ventricular conduction delay.

22. The system of claim 21 wherein the pulse pressure optimization algorithm is selected in preference to the myocardial contractility maximizing algorithm when a relatively large degree of ventricular asynchrony exists.

23. The system claim 22 wherein a large degree of ventricular asynchrony is indicated by a QRS duration interval greater than 160 milliseconds.

24. The system of claim 21 wherein the contractility maximizing algorithm is selected when the QRS interval duration is classified as short.

25. The system of claim 24 wherein the contractility maximizing algorithm is selected when the QRS interval duration is classified as medium and a lead of the pulse generator is located in the anterior cardiac vein.

26. The system of claim 25 wherein the pulse pressure optimization algorithm is selected if the QRS interval duration is classified as long.

27. The system of claim 26 wherein the contractility maximizing algorithm, if successful, recommend biventricular pacing with zero offset if the QRS interval duration is classified as short.

28. The system of claim 27 wherein successful execution of the pulse pressure optimization algorithm results in recommendations for chambers to be paced and for the programmed AV delay.

29. The system of claim 28 wherein the pulse pressure optimization algorithm and the contractility maximizing algorithm are both selected if the QRS interval duration is classified as long and neither the right ventricle is the sole paced chamber nor is the LV offset greater than zero.

30. The system of claim 16 wherein the selection of a parameter optimization algorithm is further based upon whether the parameter settings recommended by an algorithm are within acceptable ranges.

31. The system of claim 16 wherein the cardiac algorithm optimizer is implemented as software executed by an external programmer.

32. The system of claim 16 wherein the cardiac algorithm optimizer is implemented as software executed by the controller.

* * * * *